US 11,696,844 B2

(12) United States Patent
Stebbins

(10) Patent No.: US 11,696,844 B2
(45) Date of Patent: Jul. 11, 2023

(54) ROTATOR CUFF EXERCISE DEVICE

(71) Applicant: Richard Stebbins, Greenwich, CT (US)

(72) Inventor: Richard Stebbins, Greenwich, CT (US)

(*) Notice: Subject to any disclaimer, the term of this patent is extended or adjusted under 35 U.S.C. 154(b) by 0 days.

(21) Appl. No.: 16/849,897

(22) Filed: Apr. 15, 2020

(65) Prior Publication Data

US 2020/0323673 A1 Oct. 15, 2020

Related U.S. Application Data

(60) Provisional application No. 62/834,339, filed on Apr. 15, 2019.

(51) Int. Cl.
*A61F 5/01* (2006.01)

(52) U.S. Cl.
CPC .... *A61F 5/0102* (2013.01); *A61F 2005/0137* (2013.01)

(58) Field of Classification Search
CPC .. A61F 5/0102; A61F 2005/0137; A61F 5/01; A61F 5/3738; A61F 5/373; A61F 5/013; A61F 2005/0153; A61F 2005/0158; A61F 2005/0179; A61F 2005/0167; A61F 2005/0151
USPC .......................................................... 602/1
See application file for complete search history.

(56) References Cited

U.S. PATENT DOCUMENTS

| | | | |
|---|---|---|---|
| 2012/0071256 A1* | 3/2012 | Shew | A63B 69/3608 473/213 |
| 2015/0073323 A1* | 3/2015 | Begon | A61F 5/3753 602/20 |
| 2015/0337892 A1* | 11/2015 | Gräber | F16C 11/0652 403/144 |
| 2018/0193180 A1* | 7/2018 | Bejarano | A61F 5/0102 |
| 2018/0250151 A1* | 9/2018 | Kaminsky | A61F 5/01 |

* cited by examiner

*Primary Examiner* — Ophelia A Hawthorne
*Assistant Examiner* — Michael Milo
(74) *Attorney, Agent, or Firm* — TaeRa Franklin; Eckert Seamans Cherin & Mellot, LLC

(57) ABSTRACT

An apparatus is designed to provide support and correct form in order to perform rotator cuff strengthening exercises, either for rehabilitation or prevention of injury. In an exemplary embodiment, a cuff holds a person's elbow fixed at a position substantially perpendicular to curved plate secured to and parallel to a person's vertical (i.e., longitudinal) axis at the person's torso, which helps isolate internal and external rotation of the humerus and reduce any compensatory motions that can occur when the elbow is not supported. This optimally strengthens these important shoulder movements which in turn allows athletes to improve their upper extremity strength.

8 Claims, 5 Drawing Sheets

ROTATOR CUFF EXERCISE DEVICE

CROSS REFERENCE TO RELATED APPLICATIONS

This application claims priority to U.S. Provisional Patent Application No. 62/834,339, filed Apr. 15, 2019, the disclosure of which is incorporated herein by reference in its entirety.

INTRODUCTION

The apparatus disclosed herein are generally directed to exercise and physical therapy equipment, more particularly to equipment for strengthening the human rotator cuff.

SUMMARY OF INVENTION

An apparatus is designed to provide support and correct form in order to perform rotator cuff strengthening exercises, either for rehabilitation or prevention of injury. It holds the elbow fixed at a position substantially perpendicular to a person's vertical (i.e., longitudinal axis), which helps isolate internal and external rotation of the humerus and reduce any compensatory motions that can occur when the elbow is not supported. This optimally strengthens these important shoulder movements which int turn allows athletes to improve their upper extremity strength.

BRIEF DESCRIPTION

FIGS. 1A, 1B, 1C, and 1D are exemplary illustrative diagrams of an exercise apparatus, in accordance with various embodiments;

DETAILED DESCRIPTION

FIGS. 1A, 1B, 1C, and 1D are exemplary illustrative diagrams of an exercise apparatus, in accordance with various embodiments. Apparatus 100 includes two main components: a forearm cuff 110 and a pelvic plate 120. Forearm cuff 110 may be worn on a person's forearm and be secured to the person's forearm and upper arm using various securing means, including, but not limited to, an elastic, an adhesive, Velcro®, or a hook.

The orientation of cuff 110 may be greater than or less than 90 degrees in relation to the pelvic plate 120. When a person wears the exercise apparatus, the forearm of the person fits into the cuff such that their forearm forms a substantially 90 degree angle with their humerus. Accordingly, cuff 110 may be secured at an angle of greater than or less than 90 degrees in relation to the person's torso. In doing so, a wearer's range of motion may be limited to rotating along a person's vertical (i.e., longitudinal) axis according to the wearer's humerus. In this way, cuff 110 and plate 120 may create fixed angles at the elbow and shoulder, and pelvic plate 120 may be lined with padding for comfort as it is secured against the person's torso.

Figure 1A:
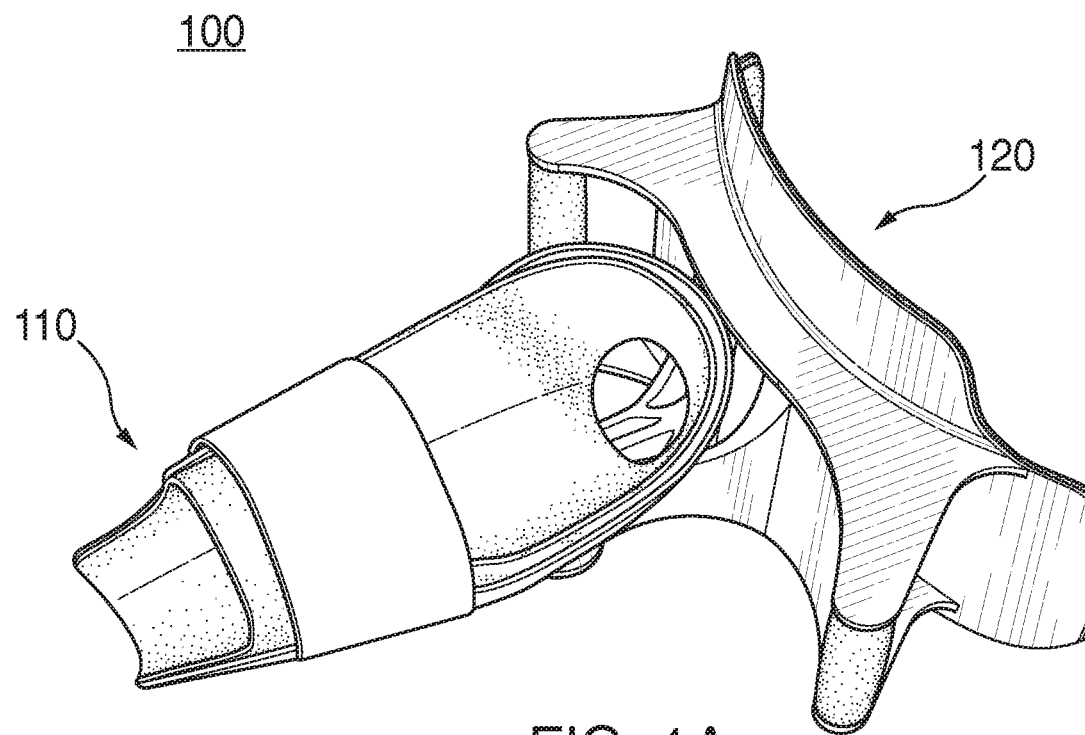
Figure 1B:
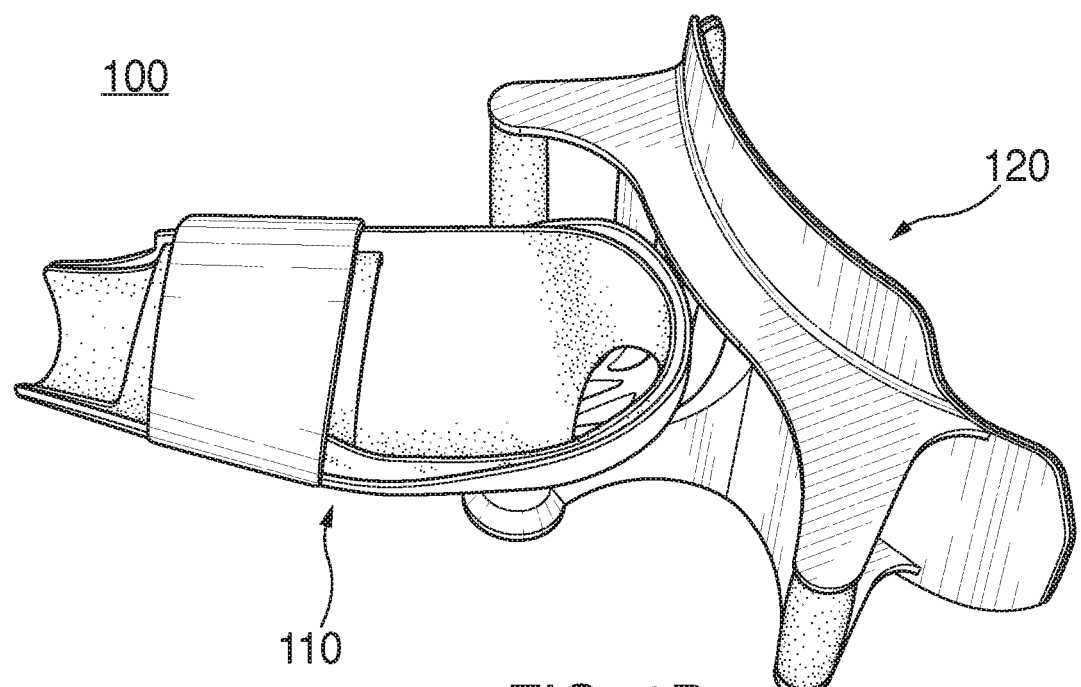
Figure 1C:
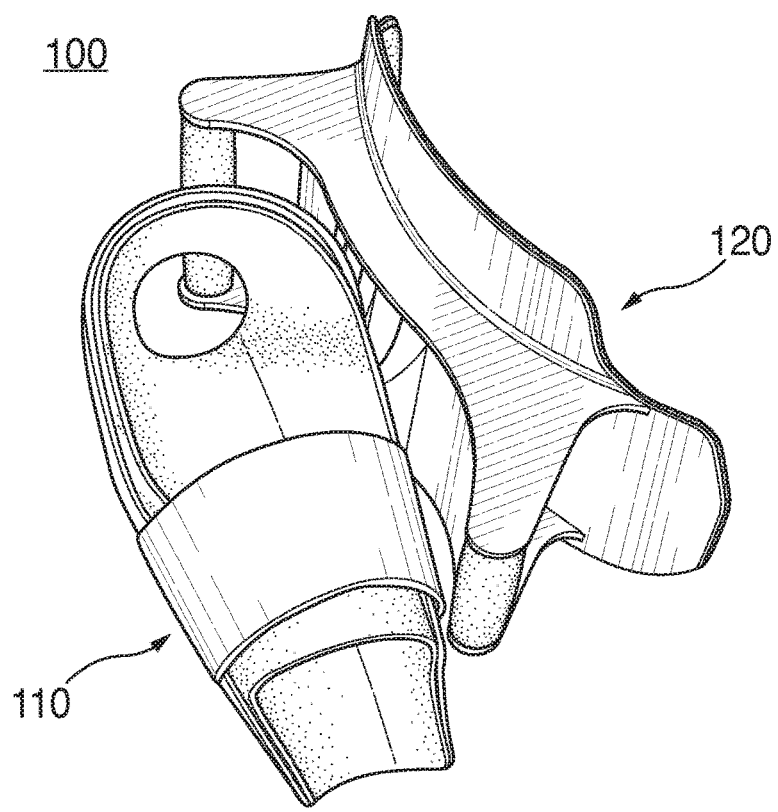
Figure 1D:
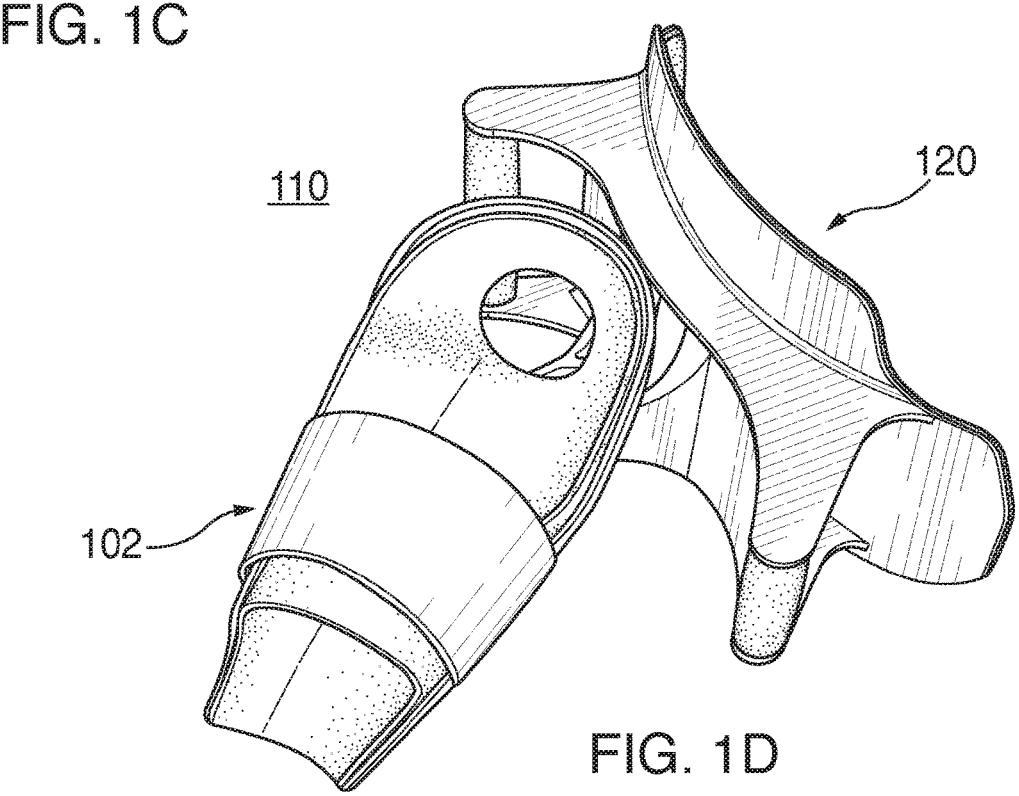
Figure 2:
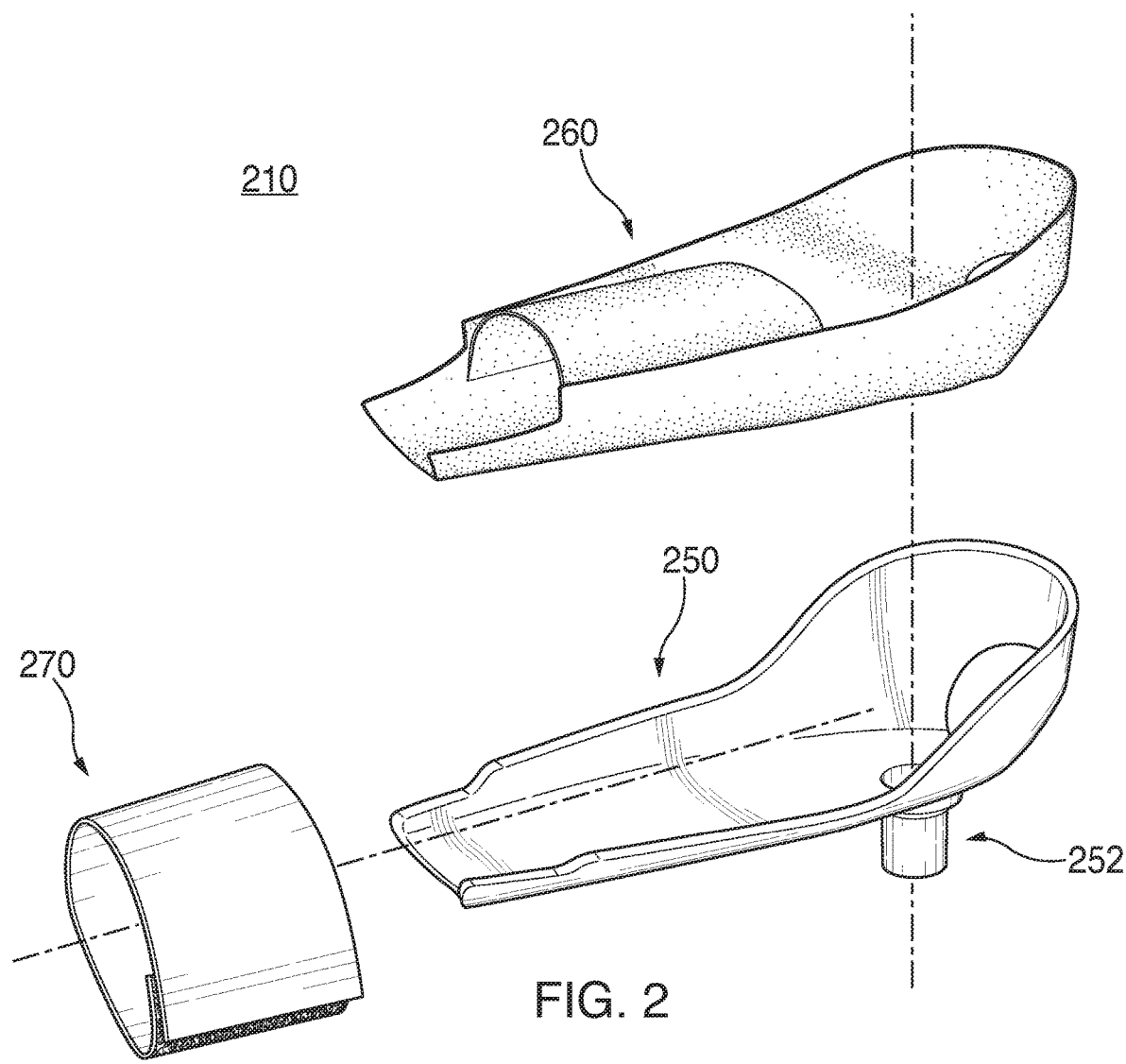
FIG. 2 is an illustrative diagram of multiple components of a cuff, in accordance with various embodiments.

FIG. 2 is an illustrative diagram of multiple components of a cuff, in accordance with various embodiments. As shown in FIG. 2, a forearm cuff 210 may include a base 250 having a post 252, a sleeve 260, and a strap 270. In some embodiments, sleeve 260 may be formed intrinsically with base 250, coupled to base 250 using adhesive, rivets, Velcro, or some other coupling means, or not coupled to base 250 at all. In some embodiments, two fixtures may be secured at the distal end of sleeve 260 to attach resistance bands, weights, or any other apparatus to provide resistance. In other embodiments, the wearer may also hold a tubing (e.g., an elastic tubing), a free weight, or some other apparatus for resistance.

In some embodiments, a post 252 may protrude from the bottom of base 250 to act as a pivot upon which the wearer rotates the cuff. This may act to provide the axis of rotation that allows for proper performance of an exercise. In some embodiments, a lip may be included at the bottom of post 252 to keep the apparatus from decoupling, moving, or otherwise "pistoning" during exercise. This post may be placed into a female trough on the pelvic plate (e.g., trough 352) for it to rotate smoothly on its axis. This axis may be lined directly with the center of rotation of the humerus of the wearer to have proper biomechanical rotation through the upper arm. This may allow the rotator cuff muscles to work optimally.

In some embodiments, this post may not be fixed in the trough. In some embodiments, the post may be held in place by the wearer contracting their scapular stabilizing muscles. This benefits the wearer in at least two ways: it may strengthen the scapular stabilizer neuromuscular motor patterns and strengthens these muscles, and if the wearer is not contracting these muscles correctly, the plate may drop to the ground giving the wearer biofeedback to use the cuff correctly.

Cuffs 110, 210, and 410 may be worn on a person's forearm and be secured to the forearm and upper arm using any means for securing (e.g., straps, adhesives, Velcro®, hooks, etc.) to fit snuggly. Cuffs 110, 210, and 410 may extend upwards along a person's vertical axis (i.e., extend toward a person's forearm and upper arm, creating an angle of approximately 90 degrees at the person's elbow) and be lined with padding for comfort. At the distal end of the forearm piece may be two fixtures to attach resistance bands to provide resistance. A person may also hold a tubing or a free weight in their hand for the desired resistance.

In some embodiments, a post may protrude from one end of cuffs 110, 210, and 410 to act as a pivot on which the wearer may rotate the cuff. This may thus provide an optimal axis of rotation to perform the exercise correctly. At the bottom of the post may be a portion that extends radially upon coupling with the plate in order to prevent decoupling and to keep the apparatus from "pistoning" during exercise.

In some embodiments, the post may fit into a female trough on the pelvic plate such that the cuff rotates smoothly on the axis of the post. This axis may be lined directly with the center of rotation of the humerus of the wearer to have proper biomechanical rotation through the upper arm. However, in some embodiments, this post may not be fixed in the trough, but rather be held in place by the wearer contracting their scapular stabilizing muscles. This may provide two benefits: it may strengthen the scapular stabilizer neuromuscular motor patterns and associated muscles, and if the wearer is not contracting these muscles correctly, the plate may drop to the ground, thereby giving the wearer biofeedback to use the cuff correctly.

Figure 3:
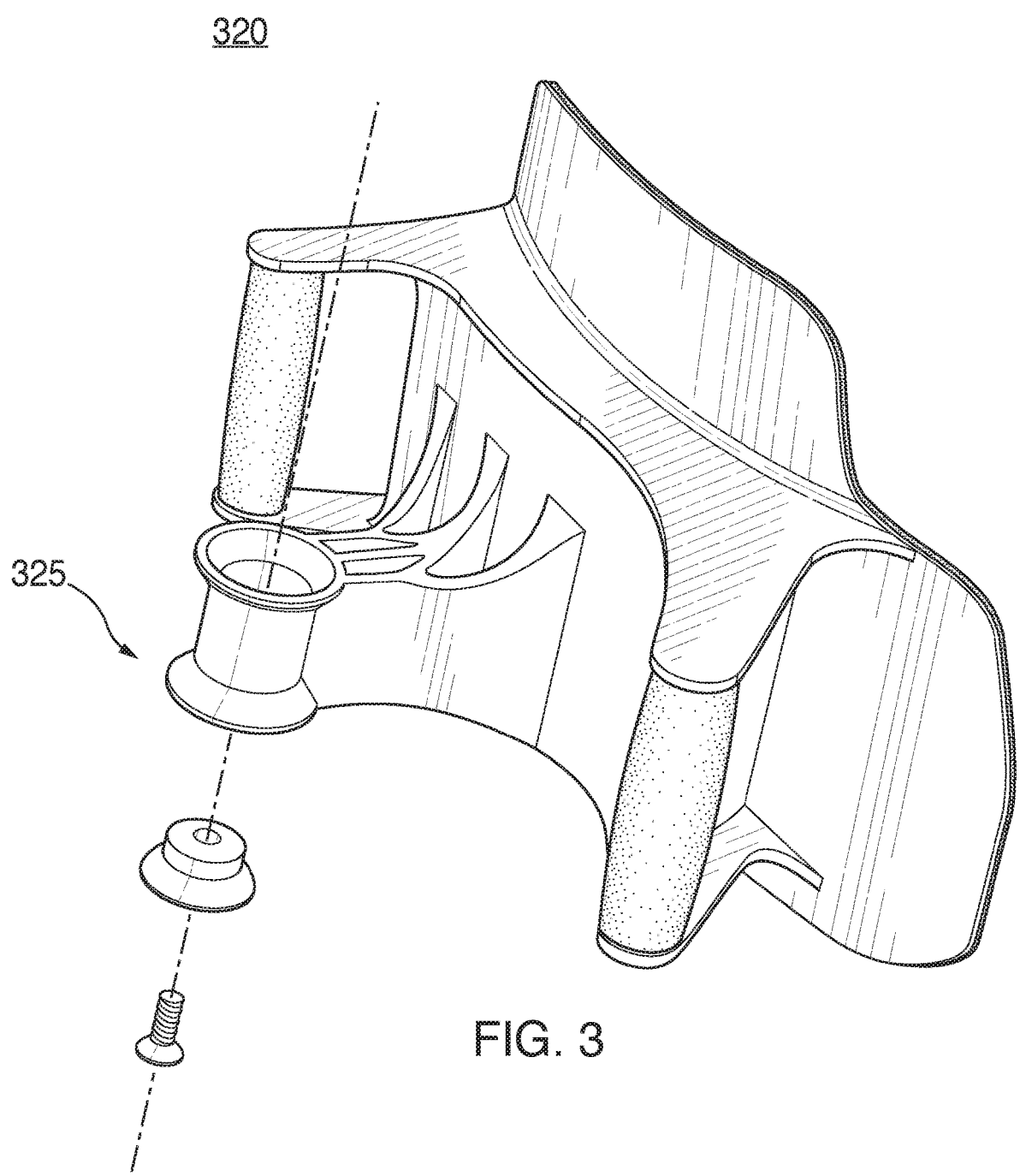
FIG. 3 is an illustrative diagram of multiple components of a pelvic plate, in accordance with various embodiments.

FIG. 3 is an illustrative diagram of multiple components of a pelvic pad, in accordance with various embodiments. The plate may be vary in thickness, be coupled to an adjustable pad, or may be operable to reversibly couple to various pads of varying thicknesses such that an angle formed between a person's humerus and torso may vary between approximately one degree and 90 degrees. An extension 325 may be located at the middle of the outside of the plate to accommodate the pivot post of the forearm cuff. This thereby may create a fixed pivot point at a reasonable distance from the person's torso, allowing the wearer to perform the exercises correctly and comfortably. In an embodiment, plate 320 may be located on the wearer's pelvic/hip area. The plate may be coupled to the cuff such that the cuff may rotate unimpeded during internal and external rotational movements of the arm. In some embodiments, the plate may include a soft but firm padding for comfort.

Figure 4:
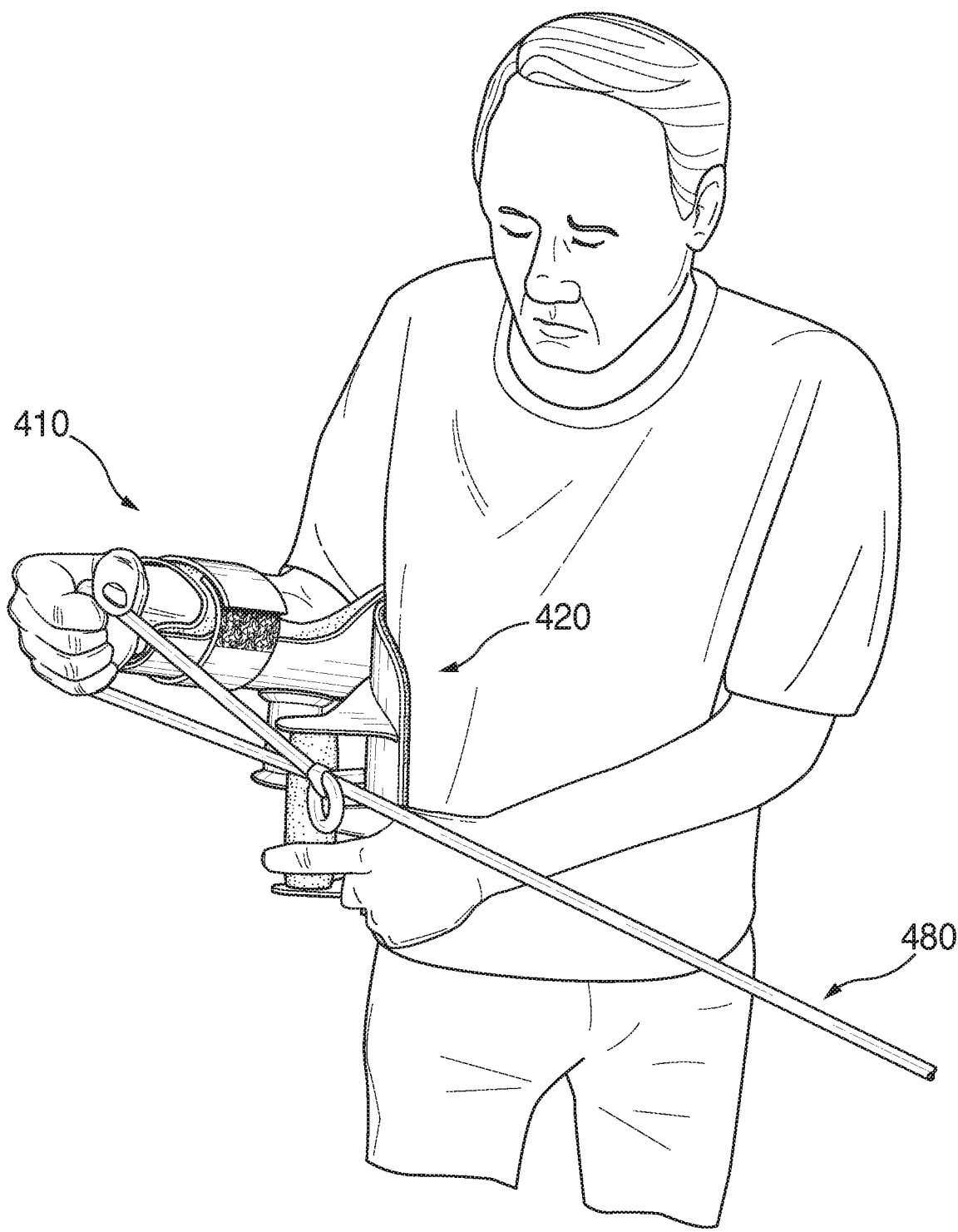
FIG. 4 is an illustrative diagram of an exercise apparatus being operated by a person, in accordance with various embodiments.

FIG. 4 is an illustrative diagram of an exercise apparatus being operated by a person, in accordance with various embodiments. In FIG. 4, a person may be wearing the cuff 410 and plate 420 apparatus while performing an external rotation of the humerus using a resistance band 480. In some embodiments, to provide resistance, the wearer can hold free weights or resistance bands, or may hook resistance bands to forearm portion of the cuff on the hooks provided. In some embodiments, a cuff (e.g., cuffs 110, 210, and 410) may be coupled to plate 120, 320, and 420 via a spring that may provide internal resistance (as opposed to the external resistance created by a tubing or free weight) to any rotation of the cuff. In some embodiments, the spring may be located at the pivot post (i.e., the joint at which the cuff is coupled to the plate).

In an embodiment, a wearer may fix the exercise apparatus to the arm as shown in FIG. 4 and place the pelvic plate against their pelvis or hip. The plate may be held in place by inserting the pivot post in the trough of the plate. The wearer may then engage their scapular muscles to do this. While holding the plate in place, the wearer may then hold a resistance band, free weight, etc., and begin rotating their forearm on the axis of the post, which may aligned with the axis of rotation of the humerus. The wearer can perform both internal and external rotation by holding the resistance in opposite directions.

The apparatuses disclosed herein can be used at any angle the wearer deems desirable. In one embodiment, an angle may be substantially 90 degrees between the abduction shoulder angle, which may be helpful to pitchers seeking to increase their pitching strength. In such embodiments, the plate may be placed on a table and the pivot post may be inserted into the plate while the wearer is either standing or sitting to perform the exercises. In another embodiment, a person may lie on their side or stomach and perform external rotation using a free weight for resistance.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An apparatus, comprising:
a plate comprising an internal side configured to be secured against a torso of a person, an external side opposite the internal side, and a female trough extending outwardly and vertically from middle of a lower portion of the external side, the female trough having a cylindrical shape;
a forearm cuff comprising a base and a sleeve formed within the base and configured to secure a forearm of the person, the base having a cylindrical post configured to be placed into the female trough of the plate, the forearm cuff rotatably coupled to the plate via the post, wherein the forearm cuff is operable to rotate along the person's vertical axis of rotation and the post is configured to act as a pivot upon which the person rotates the forearm cuff, wherein the post is not fixed within the female trough, wherein the post is held in place when scapular stabilizing muscles of the person are contracted;
wherein when the apparatus is secured to an elbow of an arm of the person, the forearm of the arm of the person forms a fixed angle between eighty-five degrees and ninety-five degrees with a humerus of the arm of the person, the torso of the person forming a fixed angle with the humerus, the angle being less than ninety degrees, and wherein movement of the person's arm is limited such that rotation of the forearm cuff follows a rotation of the person's humerus such that movement of the person's arm is limited to perform at least one of an internal rotation and an external rotation of the humerus.

2. The apparatus of claim 1, wherein the plate is configured to provide feedback to the person on correct usage of the apparatus.

3. The apparatus of claim 2, wherein the plate is configured to drop to the ground when the user is not contracting the scapular stabilizing muscles as the feedback.

4. The apparatus of claim 1, further comprising a strap for securing the person's arm into the forearm cuff.

5. The apparatus of claim 1, further comprising a belt for securing the plate against the person's torso.

6. The apparatus of claim 1, further comprising padding coupled to the internal side, wherein the plate is coupled to the forearm cuff at the external side.

7. The apparatus of claim 1, wherein the forearm cuff comprises a first end and a second end, wherein the first end comprises a strap for securing at least the person's forearm and wrist to the forearm cuff, and wherein the second end extends parallel along the person's vertical axis to secure the person's elbow.

8. The apparatus of claim 1, wherein the forearm cuff and the plate form an angle between sixty degrees and ninety degrees.

\* \* \* \* \*